(12) United States Patent
Treuth

(10) Patent No.: US 7,420,193 B2
(45) Date of Patent: Sep. 2, 2008

(54) RADIATION SHIELD

(76) Inventor: Mark G. Treuth, 5432 Woodbine La., Salisbury, MD (US) 21801

(*) Notice: Subject to any disclaimer, the term of this patent is extended or adjusted under 35 U.S.C. 154(b) by 232 days.

(21) Appl. No.: 11/462,394

(22) Filed: Aug. 4, 2006

(65) Prior Publication Data

US 2007/0029513 A1 Feb. 8, 2007

Related U.S. Application Data

(60) Provisional application No. 60/705,860, filed on Aug. 5, 2005.

(51) Int. Cl.
*G21F 3/02* (2006.01)
*G21F 3/00* (2006.01)
*A61B 6/10* (2006.01)

(52) U.S. Cl. .............. 250/519.1; 250/515.1; 250/516.1; 250/505.1

(58) Field of Classification Search ............. 250/519.1, 250/515.1, 516.1, 505.1
See application file for complete search history.

(56) References Cited

U.S. PATENT DOCUMENTS 6,583,420 B1 * 6/2003 Nelson et al. ............... 250/397
7,291,841 B2 * 11/2007 Nelson et al. ........... 250/370.09

* cited by examiner

*Primary Examiner*—Nikita Wells
(74) *Attorney, Agent, or Firm*—Connolly, Bove, Lodge & Hutz

(57) ABSTRACT

A radiation shield includes a radio-opaque drape which has an open area extending completely through the drape to provide a viewing site. Radiation control structure in the form of a vent system is located in the open area. The vent system includes a plurality of radio-opaque slats extending at least partially across at least a portion of the open area. The slats preferably extend outwardly away from the surface of the drape to facilitate the capturing of scattered radiation.

17 Claims, 1 Drawing Sheet

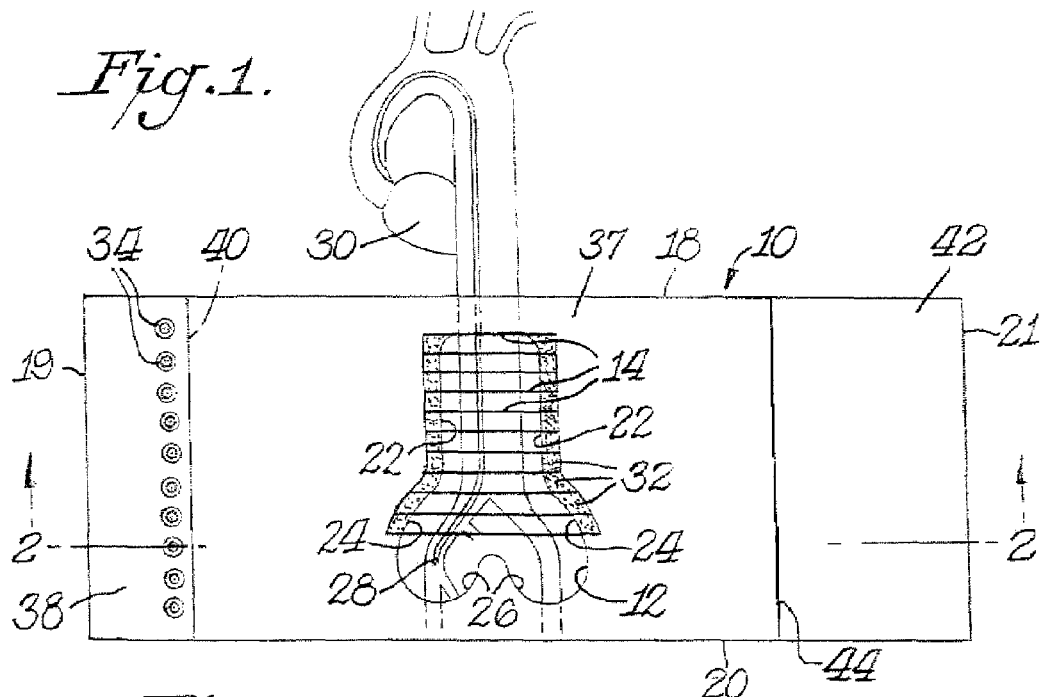
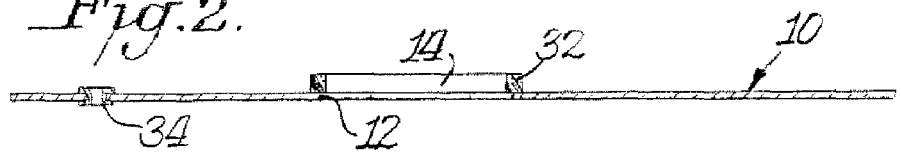
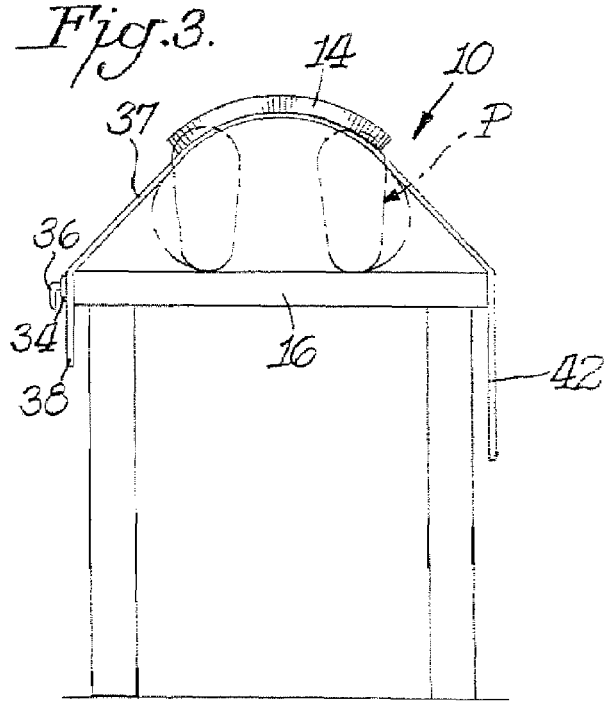

RADIATION SHIELD

CROSS-REFERENCE TO RELATED APPLICATION

This application is based on provisional application Ser. No. 60/705,860 filed Aug. 5, 2005.

BACKGROUND OF THE INVENTION

Cardiac imaging uses an x-ray source under the patient that emits x-rays which travel through the x-ray table and the patient to above the table imager. In such procedures x-rays are used, for example, during a cardiac cathertization procedure to image the coronary arteries. The drawback with this arrangement is that the radiation can be redirected or scattered like a bullet that ricochets. While the patient is rarely exposed to radiation, the cath lab personnel are exposed to radiation from the scattered radiation. For one procedure the scattering does not result in a lot of exposure. Over the years, however, the exposure is great.

Current methods include shields that move in front of the cath lab personnel. The drawback with these methods, however, is that it is difficult to see the patient. In addition, because the shields are bulky they are frequently not used. Further, such shields do not block the radiation well. Current shielding techniques consist of an under the table drape and a movable lead shield. Shielding that could be draped over the patient from the abdomen to the leg would decrease the exposure to cath lab personnel. Unfortunately, the catheters, however, need to be viewed as they pass through the aorta and simply placing a lead shield over the patient would block view of the catheters.

SUMMARY OF THE INVENTION

An object of this invention is to provide a radiation shield which blocks scattered radiation to the cath lab personnel, but permits direct visualization of the catheters.

A further object of this invention is to provide such a radiation shield which would decrease radiation exposure to the cath lab staff while still providing less of an obstructed view of the patient.

In accordance with this invention a lead or radio-opaque drape is placed over the patient. The drape includes an open area which would comprise a viewing site. Radiation control structure in the form of a plurality of spaced radio-opaque slats extends at least partially across at least a portion of the open area. The provision of the slats in the open area forms what may be considered as a vent having the dual functions of blocking scattered radiation while still permitting viewing of the catheters as they pass through the aorta.

In a preferred practice of this invention the slats extend outwardly and preferably generally perpendicularly to the surface of the drape. The open area may be shaped to generally conform to the shape of the anatomy in question thereby minimizing the size of the open area. The slats would extend completely across the open area in a confined portion of the open area thereby leaving a completely exposed portion for viewing purposes.

THE DRAWINGS

FIG. 1 is a top plan view in use of a radiation shield in accordance with this invention;

FIG. 2 is a side elevational view of the shield shown in FIG. 1;

FIG. 3 is a side elevational view of the shield shown in FIGS. 1-2 during use; and FIG. 4 is a perspective view of a slat used as part of the vent structure in the shield of FIGS. 1-3.

DETAILED DESCRIPTION

In a preferred practice of the invention, such as illustrated in FIGS. 1-4, the radiation shield comprises a radio-opaque drape 10 made of any suitable radiation-opaque material, such as lead. The drape 10 includes a cut-out 12 having radiation control structure located in a portion of the open area 12 to minimize exposure to scattered radiation. Preferably, the radiation control structure is in the form of a vent having a plurality of radio-opaque slats 14 extending at least partially across at least a portion of the open area 12. Cut-out or open area 12 is located, for example, at about the center of the drape 10 so that it is properly disposed at the patient when the patient is lying on a table 16 as shown in FIG. 3.

In the specifically illustrated practice of this invention the radiation shield is intended to function in connection with cardiac imaging where it is desired to view catheters as they pass through the aorta. In order to minimize the size of the open area 12 the cut-out or open area may be shaped to closely conform to the anatomy of the patient in, for example, the area extending from the abdomen to the legs or from the chest to the abdomen. It is to be understood, however, that the invention may be practiced for use in other techniques which would involve the need to view a portion of the patient thereby making use of the cut-out or open area while providing the open area with the radiation control structure or radio-opaque vent.

In a preferred practice of this invention when the invention is used in connection with cardiac imaging, each slat 14 extends outwardly from the surface of drape 10, preferably perpendicular to the surface of drape 10 and is about 1 inch high with adjacent slats being separated from each other by a distance of about 1 inch. Thus, there is about a 1:1 ratio of height to separation. It is to be understood, however, that the invention could be practiced with other dimensions and ratios. Similarly the slats could extend outwardly from the surface of the drape at a non-perpendicular angle.

In the illustrated embodiment shown in FIG. 1 the drape 10 is generally rectangular in shape having a trans-verse upper edge 18 and a transverse lower edge 20 interconnected by shorter longitudinal edges 19,21 with the open area or cut-out 12 longitudinally disposed between these edges. Preferably cut-out 12 is centrally located in the drape. Where the invention is practiced for cardiac imaging the open area 12 takes the shape of a pair of generally parallel edges 22 joined at one end by a straight edge. At the opposite end, edges 22 merge outwardly at 24 and with the portion of cut-out 12 near the lower edge 20 of drape 10 having bifurcations 26 merging from the outwardly extending portions 24. The bifurcated portions provide catheter insertion sites. Thus, for example, a catheter 28 could be inserted into the patient at one of the bifurcations 26. In this manner the catheter 28 is placed into the body of the patient and viewed using radiographic observation or fluoroscopy. The catheter 28 which would be a coronary catheter which extends from the insertion site to the heart 30. By shaping the cut-out or open area 12 to correspond to the anatomy of concern, the size of the open area is minimized. The vent structure created by the slats 14 is located in the portion of the open area upwardly from the bifurcated portions. In other words, the slats 14 are located in the portion of the cut-out comprising the parallel edges 22 and the outwardly extending edges 24. As a result, the bifurcated portions 26 remain exposed to provide ready access to the catheter insertion sites.

The system created by slats 14 allows the catheter 28 to be viewed but the cath lab staff would be shielded from the scattered radiation because the radiation control structure or vent system would block the radiation. The only radiation going through the shield or drape 10 would be straight through to the imager. Scattered radiation would be captured by the vent/slats 14. This works for anterior-posterior views. The shield would stop below the heart 30 since the heart needs to be viewed in multiple angles. Most of the scattered radiation should still be captured as it could not penetrate the shield and any scatter from that area would be less intense because it would be farther from the source since radiation intensity declines exponentially with distance.

In practicing the invention provisions should be made with regard to the imager being occasionally directed toward the cath lab staff. Such provisions, in addition to the cover shielding provided by the radiation shield of this invention would also include a radio-opaque "donut" around the imager. Such donut could be, for example, a six inch wide circular shield which could be attached to the drape 10. This would block x-rays when the imager is directly in front of the cath lab staff and the x-ray tube is pointed directly at them.

In a preferred practice of the invention the spacing and positioning of the slats 14 is enhanced by the provision of spacers 32 which may be made of any suitable material such as foam. The foam spacers are located at the periphery of cut-out or open area 12 along edges 22 and 24. As noted, each slat 14 is preferably about one inch high and adjacent slats are spaced apart a distance of about one inch. The slats themselves may be about ⅛ inch thick and made from a radio opaque material which preferably is bendable in a transverse direction, i.e. along the length of the slat. Thus, as shown in FIG. 3 when the drape 10 is disposed over the patient and extend downwardly along the sides of the table 16 thereby generally forming an arc, the slats 14 conform to the shape of the arc.

The radiation shield may be mounted around the patient in any suitable manner. For example, FIGS. 1-2 illustrate the drape 10 to include a plurality of spaced reinforced holes or grommets 34 generally at one end of the drape 10. The table 16 could preferably include a plurality of hooks 36 located at one side edge of the table 16. When the patient P lies on the table one end of the drape 10 would be anchored to the table by inserting the hooks 36 through the grommets 34. The provision of the grommets also permits the longitudinal positioning of the drape 10 on the patient to be adjusted, in addition to comprising mounting structure for anchoring the drape 10 to the table 16. Although FIGS. 1-3 illustrate the mounting and adjusting structure to be in the form of grommets which cooperate with hooks, any other suitable mounting/adjusting structure could be used.

In the preferred practice of the invention each slat 14 extends completely across the open area 12 in a transverse direction. It is to be understood, however, that the invention may also be practiced where the slats extend only partially across the open area and/or where some or all of the slats extend in a longitudinal or oblique direction.

As noted drape 10 could be of any suitable size and shape. Preferably, the drape is of rectangular shape having a central panel 37 which is located between the edges of the supporting surface of table 18 with one end panel 38 located at the anchored end of drape 10 created along hinge line 40 and with a further end panel 42 extending downwardly from table 16 at its hinge line 44. The intermediate portion 37 of drape 10 would be disposed over the patient between hinge lines 40 and 42. Other shapes may, however, be used for drape 10 as considered appropriate or desirable including providing longitudinal extensions to cover portions of the patient's body beyond the edges 18 and/or 20. Depending upon the intended use of drape 10, the longitudinal dimension upper edge 18 could extend to the chest area of the patient while lower edge 20 could extend to the abdominal area or the edge 18 could be at the abdominal area, while the lower edge 20 is at the leg area.

FIG. 1 illustrates the open area to include bifurcated portions 26,26 at a location downwardly of the vent structure having slats 14. This minimizes the size of the cutout or open area that remains exposed to provide access to the patient. The exposed portion, however, need not be bifurcated but could terminate in a smooth edge extending inwardly from the outward edges 24,24. The cut-out or open area 12 could, for example, simply be of oval shape or rectangular shape. The various slats 14 could form any pattern to create the vent structure. Thus, for example, as illustrated the slats 14 are equally spaced parallel to each other extending in a transverse direction. If desired, however, the slats could extend in a longitudinal direction or could be oblique or could form a grid pattern comprising a combination of longitudinal and/or transverse and/or obliquely arranged slats. In addition the slats need not be uniformly spaced apart.

It should be apparent that given the teachings of this invention the radiation shield could take various forms. One of the key features, however, is the provision of an open area which incorporates radiation control structure such as a vent system in the form of a plurality of spaced radio-opaque slats. The slats function to block scattered radiation which would be directed along the surface of the outwardly extending slats and would be prevented from being directed toward cath lab personnel or other personnel in the vicinity of the patient. Although drape 10 is flexible in the sense of being able to bend around a patient in a conventional manner, the drape 10 could be made of a more rigid radio-opaque material having, for example, a generally horizontal section that would be disposed directly above the patient and having downwardly extending rigid sides that would extend toward the table. Such structure would form a three-sided box-like formation that would be disposed over the patient. Other variations in the practice of this invention would also be apparent to one of ordinary skill in the art giving the teachings and suggestions of this invention.

What is claimed is:

1. A radiation shield comprising a radio-opaque drape, an open area completely through a portion of said drape to comprise a viewing site, radiation control structure in said open area to minimize exposure to scatter radiation, and said radiation control structure comprising a vent in the form of a plurality of spaced radio-opaque slats extending at least partially across at least a portion of said open area.

2. The shield of claim 1 wherein said slats extend outwardly away from the surface of said drape to facilitate the capturing of scatter radiation.

3. The shield of claim 2 wherein each of said slats extends in a generally vertical direction substantially perpendicular to the surface of said drape.

4. The shield of claim 2 including spacers located between adjacent pairs of said slats along the periphery of said open area where said slats are located.

5. The shield of claim 4 wherein said spacers are made from a foam material.

6. The shield of claim 2 wherein each of said slats has a height which is substantially the same as the spacing between pairs of adjacent slats.

7. The shield of claim 2 wherein said drape includes adjustable mounting structure for adjustably mounting said drape to a support table.

8. The shield of claim 7 wherein said open areas includes a portion free of said slats to remain exposed and provide access to the patient through said portion of said open area.

9. The shield of claim 8 wherein said drape is flexible, and each of said slats is bendable to conform to the shape of said drape when said drape is placed on a patient.

10. The shield of claim 2 wherein said open areas includes a portion free of said slats to remain exposed and provide access to the patient through said portion of said open area.

11. The shield of claim 10 wherein said open area comprises a pair of generally parallel edges which merge into outwardly extending edges which merge into said exposed portion.

12. The shield of claim 11 wherein said exposed portion is of bifurcated shape.

13. The shield of claim 12 wherein each of said slats extends completely transversely across said open area parallel to each other.

14. The shield of claim 13 wherein said drape is generally rectangular in shape having a pair of longitudinal edges connected by a pair of transverse edges and said longitudinal edges being shorter than said transverse edges, one of said transverse edges being an upper edge, the other of said transverse edges being a lower edge, said parallel edges of said open area being in the general area of said upper edge, and said exposed portion of said cut-out being generally at said lower edge.

15. The shield of claim 14 wherein said open area is generally located at the center of said drape.

16. The shield of claim 2 wherein each of said slats is bendable along its length.

17. A method of shielding personnel from scatter radiation wherein a drape is mounted over a patient who is exposed to radiation including providing an open area in a portion of the drape which includes a corresponding portion of the patient's anatomy having catheter sites, providing a vent system in the radio-opaque drape across at least a portion of the open area with the vent system comprising a plurality of spaced radio-opaque slats extending outwardly from the surface of the drape and leaving a portion of the open area exposed at the catheter sites, and utilizing the vent system to block scattered radiation.

\* \* \* \* \*